(12) United States Patent
Mordant (10) Patent No.: US 12,178,952 B2
(45) Date of Patent: Dec. 31, 2024

(54) INJECTION CANNULA, ECMO SYSTEM (71) Applicant: ASSISTANCE PUBLIQUE HOPITAUX DE PARIS, Paris (FR)

(72) Inventor: Pierre Mordant, Paris (FR)

(73) Assignee: Assistance Publique Hopitaux de Paris, Paris (FR)

( * ) Notice: Subject to any disclaimer, the term of this patent is extended or adjusted under 35 U.S.C. 154(b) by 669 days.

(21) Appl. No.: 17/310,112

(22) PCT Filed: Jan. 21, 2020

(86) PCT No.: PCT/EP2020/051350
§ 371 (c)(1),
(2) Date: Jul. 16, 2021

(87) PCT Pub. No.: WO2020/156874
PCT Pub. Date: Aug. 6, 2020

(65) Prior Publication Data
US 2022/0062523 A1   Mar. 3, 2022

(30) Foreign Application Priority Data
Jan. 28, 2019 (FR) ..................................... 1900752

(51) Int. Cl.
*A61M 1/36* (2006.01)
*A61L 29/08* (2006.01)
*A61M 1/16* (2006.01)

(52) U.S. Cl.
CPC ........... *A61M 1/3659* (2014.02); *A61L 29/08* (2013.01); *A61M 1/1698* (2013.01);
(Continued)

(58) Field of Classification Search
CPC .............. A61M 1/3659; A61M 1/1698; A61M 1/3623; A61M 2205/0266;
(Continued)

(56) References Cited

U.S. PATENT DOCUMENTS 5,542,936 A   8/1996 Razi
6,283,951 B1 * 9/2001 Flaherty ........... A61B 17/12172
604/164.11
(Continued)

FOREIGN PATENT DOCUMENTS

WO   2004/032791 A2   4/2004

OTHER PUBLICATIONS

International Search Report for International Patent Application No. PCT/EP2020/051350, dated May 6, 2020 in 188 pages.

*Primary Examiner* — Susan S Su
*Assistant Examiner* — Erin A Kim
(74) *Attorney, Agent, or Firm* — Knobbe, Martens Olson & Bear, LLP (57) ABSTRACT

The invention relates to a cannula (1) for injecting a fluid (F1) into a body cavity (5), comprising:
   a main lumen (LP) for the fluid to flow in a first direction;
   an accessory reperfusion lumen (LA) comprising an outlet (20') for discharging the fluid in a second direction; and
   a device for positioning the cannula in the cavity, the device comprising a stop (41) which can move along an auxiliary lumen (LX) and be deployed in the cavity in order to lock the cannula in position in the cavity,
the outlet (30') of the auxiliary lumen being arranged at a distance (d) from the outlet (20') of the accessory reperfusion lumen such that when the cannula is locked in position in the cavity, the outlet (20') of the accessory reperfusion lumen (LA) is oriented in the cavity such that the collected fluid is discharged in the second direction.

11 Claims, 5 Drawing Sheets

(52) U.S. Cl.
CPC ........ *A61M 1/3623* (2022.05); *A61L 2300/42* (2013.01); *A61M 2205/0266* (2013.01)

(58) Field of Classification Search
CPC ...... A61M 25/0029; A61M 2025/0031; A61M 25/0026; A61M 25/0075; A61M 1/366; A61M 2025/0078; A61M 2025/0076; A61M 2025/0018; A61M 2025/0293; A61M 25/0071; A61M 25/007; A61L 29/08; A61L 2300/42
See application file for complete search history.

(56) References Cited

U.S. PATENT DOCUMENTS

| | | | | |
|---|---|---|---|---|
| 2003/0187392 | A1* | 10/2003 | Hogendijk | A61M 1/7413 604/129 |
| 2005/0187578 | A1* | 8/2005 | Rosenberg | A61M 25/04 606/232 |
| 2016/0121079 | A1* | 5/2016 | Walther | A61M 25/007 604/264 |
| 2017/0100141 | A1* | 4/2017 | Morero | A61B 17/3478 |
| 2018/0236203 | A1* | 8/2018 | Franklin | A61M 25/1006 |
| 2019/0083695 | A1* | 3/2019 | Yokoyama | A61M 25/01 |

* cited by examiner

INJECTION CANNULA, ECMO SYSTEM

CROSS-REFERENCE TO RELATED APPLICATIONS

This application is the U.S. National Phase under 35. U.S.C. § 371 of International Application PCT/EP2020/051350, filed Jan. 21, 2020, which claims priority to French Patent Application No. 1900752, filed Jan. 28, 2019. The disclosures of the above-described applications are hereby incorporated by reference in their entirety.

TECHNICAL FIELD OF THE INVENTION

The technical field of the invention is that of cannulas for injecting a fluid into a cavity of the human or animal body, for example an organ, an arterial or venous blood vessel, a lymphatic vessel, or a bronchial structure.

More particularly, the invention relates to an injection cannula for an extracorporeal membrane oxygenation system, referred to as an ECMO system, and to an ECMO system comprising such an injection cannula.

TECHNOLOGICAL BACKGROUND OF THE INVENTION

Nowadays, cannulas are available that are combined with extracorporeal membrane oxygenation systems, also known as ECMO systems. In particular, an ECMO system comprises a set of components that can be used to extract a blood volume from a cavity of the human or animal body by means of an intake cannula, to oxygenate it, decarboxylate it, optionally heat it, and then reinject it, by means of an injection cannula, into a cavity different from or identical to the cavity from which it was extracted.

In particular, all kinds of cannulas are available for ECMO systems, depending on the desired applications, in particular veno-venous VV, veno-arterial VA or veno-arteriovenous VAV applications.

VA ECMO, which stands for "veno-arterial extracorporeal membrane oxygenation", i.e., veno-arterial ECMO, is a reference treatment for refractory cardiogenic shock, refractory cardiac arrest, and decompensated primary or secondary pulmonary hypertension. It is a preferred technique in the event of poor haemodynamic or respiratory tolerance of lung transplantation, heart transplantation, and any pulmonary or cardiovascular thoracic surgery.

VA ECMO is referred to as "peripheral VA ECMO" when oxygenated blood is injected into a peripheral artery and not into the aortic root or pulmonary artery (central VA ECMO). The peripheral VA ECMO circuit generally comprises an intake cannula which is preferably placed in a large-diameter vein, a centrifugal pump, an oxygenation and decarboxylation membrane and an injection cannula which is also preferably placed in a large-diameter artery, for example the axillary artery or the femoral artery.

However, the drawback of such a system lies in the placement of the arterial injection cannula in a peripheral artery because of a high risk of arterial occlusion and therefore limb ischemia. Indeed, once inserted into the artery, the injection cannula can lead to a reduction in the downstream flow rate due to the presence of the cannula and the creation of a retrograde arterial flow. The terms "downstream" and "retrograde" are defined with respect to the physiological direction of blood flow. The decrease in the downstream flow rate can thus alter the arterial perfusion flow of the limb and create limb ischemia.

In order to overcome the aforementioned drawbacks, connecting a Y-shaped second cannula referred to as a reperfusion cannula to the arterial line of the ECMO system is known. This reperfusion cannula is implanted in the anterograde direction, downstream of the main cannula, generally implanted in the retrograde direction. However, this technique has drawbacks, in particular because of the use of two cannulas of different diameters which need to be implanted at two different locations on the artery as well as in two different directions. This is therefore a lengthy and complex procedure, most often carried out in an emergency context.

Thus, a solution, described in patent application FR 1 661 037, consists in using an injection cannula that combines, in a single device, a main cannula referred to as the main lumen, and a reperfusion cannula referred to as the accessory lumen, so as to reduce the number of insertion points and thus simplify the procedure for introducing the injection cannula into the artery. In order for the fluid exiting the accessory lumen to flow in an anterograde direction, the accessory reperfusion lumen so as to collect a portion of the retrograde blood flow coming from the main lumen, then has an angled portion for reversing the direction of flow of the fluid. The fluid flowing in the accessory lumen is then discharged into the artery in the anterograde direction through an outlet port provided in the wall of the injection cannula.

In order to ensure the correct operation of such a cannula, it is essential for the outlet port of the accessory lumen to be correctly positioned in the artery. Indeed, if it is incorrectly positioned in the artery, the outlet port can:
press against the posterior wall or anterior wall of the artery, which does not allow effective reperfusion and can cause damage to the wall of the artery due to the strength of the blood flow injected against the wall (arterial dissection, thrombosis, distal embolism),
be located outside the artery and therefore be ineffective, or even cause a major subcutaneous haematoma.

SUMMARY OF THE INVENTION

The invention provides a solution to the problems mentioned above, by making it possible to correctly position the outlet port of an accessory reperfusion lumen in a cavity of the human or animal body.

A first aspect of the invention relates to a cannula for injecting a fluid into a cavity of the human or animal body, comprising:
a main lumen defining a first space of the cannula for the fluid to flow in a first direction; and
an accessory reperfusion lumen defining a second space of the cannula and comprising:
an inlet for collecting a portion of the fluid flowing in the first direction;
an angled portion for changing the direction of flow of the fluid collected by the accessory reperfusion lumen; and
an outlet for discharging the collected fluid in a second direction into the cavity.

In addition, the cannula comprises a device for positioning the cannula in the cavity, the positioning device comprising a stop and movement means configured to move said stop along an auxiliary lumen, the auxiliary lumen defining a third space of the cannula and comprising an outlet opening into the cavity. The movement means make it possible to deploy the stop in the cavity, via the outlet of the auxiliary lumen, in order to ensure that the cannula is locked in position in the cavity.

Furthermore, the outlet of the auxiliary lumen is arranged at a predetermined distance from the outlet of the accessory reperfusion lumen such that, when the stop locks the cannula in position in the cavity, the outlet of the accessory reperfusion lumen is oriented in the cavity in such a way that the collected fluid is discharged in the second direction.

The term "body cavity" should be understood to mean an organ, a blood vessel, a lymphatic vessel or a bronchial structure.

As a result of the injection cannula according to the invention, the outlet of the accessory reperfusion lumen is correctly positioned in the cavity, which makes it possible to ensure effective reperfusion of the cavity without the need for radiological or echographic control.

Furthermore, the distance between the outlet of the accessory reperfusion lumen and the outlet of the auxiliary lumen is selected according to the dimensions of the cavity such that, when the stop locks the position of the injection cannula in the cavity, the outlet of the accessory reperfusion lumen is correctly positioned in the cavity. The term "correctly positioned" should be understood to mean that the outlet of the accessory reperfusion lumen is arranged in the cavity so that the blood flow is discharged into the middle of the cavity in the second direction. In particular, the predetermined distance is chosen so that the outlet of the accessory reperfusion lumen cannot be pressed against the wall of the cavity, which would prevent effective reperfusion of the cavity. Moreover, positioning the outlet of the accessory reperfusion lumen in the cavity in this way helps avoid causing damage to the wall of the cavity due to the strength of the blood flow injected against the wall.

Furthermore, the deployed stop allows the injection cannula to be locked in position in the cavity so that there is no risk of it being removed from the body of the patient, even in the event of the patient moving. Thus, the injection cannula can be held in a patient's body for a long period of time.

Furthermore, immobilizing the injection cannula in the cavity makes it possible to ensure that the outlet of the accessory reperfusion lumen cannot be located outside the cavity and therefore be ineffective or even cause a major subcutaneous haematoma.

In addition to the features which have just been mentioned in the preceding paragraph, the injection cannula according to the first aspect of the invention may have one or more of the following complementary features, considered individually or according to all technically possible combinations:
- the predetermined distance between the outlet of the accessory reperfusion lumen and the outlet of the auxiliary lumen is between 0.1 and 500 mm;
- the movement means comprise a push-button capable of moving in a longitudinal groove provided in the cannula, the movement of the push-button in the longitudinal groove causing the stop to be moved along the auxiliary lumen via a connecting element connected to said stop;
- the deployed stop has a shape and dimensions designed to prevent the cannula from being withdrawn when said cannula is inside the cavity;
- the stop is made from a shape memory material;
- the stop is made from a nickel-titanium alloy wire;
- the deployed stop is diamond-shaped;
- the stop has an anti-thrombogenic and/or anti-proliferative coating;
- the stop and/or the outlet of the auxiliary lumen has/have a radio-opaque or echo-opaque marking designed to allow said stop and/or said outlet of the auxiliary lumen to be identified by radiography or echography; and
- a bleed valve is connected to the accessory reperfusion lumen.

A second aspect of the invention relates to a system for injecting a fluid into a cavity of the human or animal body, comprising:
- an intake cannula for receiving a predetermined fluid;
- a pump for pumping the predetermined fluid coming from the intake cannula;
- an oxygenator for oxygenating the predetermined fluid coming from an outlet of the pump; and
- an injection cannula according to the first aspect of the invention, for injecting the oxygenated fluid into the cavity.

According to one non-limiting embodiment, the injection system comprises a heat exchanger for injecting the oxygenated fluid into the injection cannula at a predetermined temperature.

The invention and its various applications will be better understood upon reading the following description and examining the accompanying figures.

BRIEF DESCRIPTION OF THE FIGURES

The figures are provided as an indication and in no way limit the invention.

The figures are provided as an indication and in no way limit the invention.

DETAILED DESCRIPTION

The invention relates to an injection cannula used to inject a fluid into a cavity of the human or animal body, for example an organ, a blood vessel, a lymphatic vessel or a bronchial structure. In particular, the injection cannula is used in an ECMO system which can be used to oxygenate a volume of fluid extracted from a cavity of the body and reinject it into a cavity different from or identical to the cavity from which it was extracted.

Hereinafter in the description, it will be assumed that the fluid to be injected into a cavity of the body is blood. In addition, the ECMO system is considered to be veno-arterial (VA), i.e., the cavity of the body from which the flow is extracted is a vein, while the cavity into which the flow is reinjected is an artery. Naturally, this embodiment is in no way limiting, it being possible for the ECMO system to be, for example, of the veno-venous (VV) type or indeed of the veno-arteriovenous (VAV) type.

Furthermore, the "anterograde direction of flow" of a fluid refers to the physiological direction S of blood flow in a vessel or an organ. Moreover, a "retrograde direction of flow" of a fluid refers to the opposite direction to the physiological direction S of blood flow in a vessel or an organ. The frame of reference is therefore taken in relation to the physiology of the human or animal body. By way of linguistic extension and for the sake of clarity of the disclosure of the embodiment, the direction of flow of the main lumen LP will be referred to as the "retrograde direction" and the direction of flow of the accessory reperfusion lumen LA as the "anterograde direction", each being considered at the outlet of the injection cannula when their direction is mentioned.

Moreover, the terms "upstream" and "downstream" are defined in the present text with respect to the practitioner handling the injection cannula according to the invention.

Finally, the term "F0" denotes a flow of untreated blood, i.e., poor in oxygen and rich in carbon dioxide, and the term "F1" denotes a flow of treated blood, i.e., oxygenated and decarboxylated.

Figure 1:
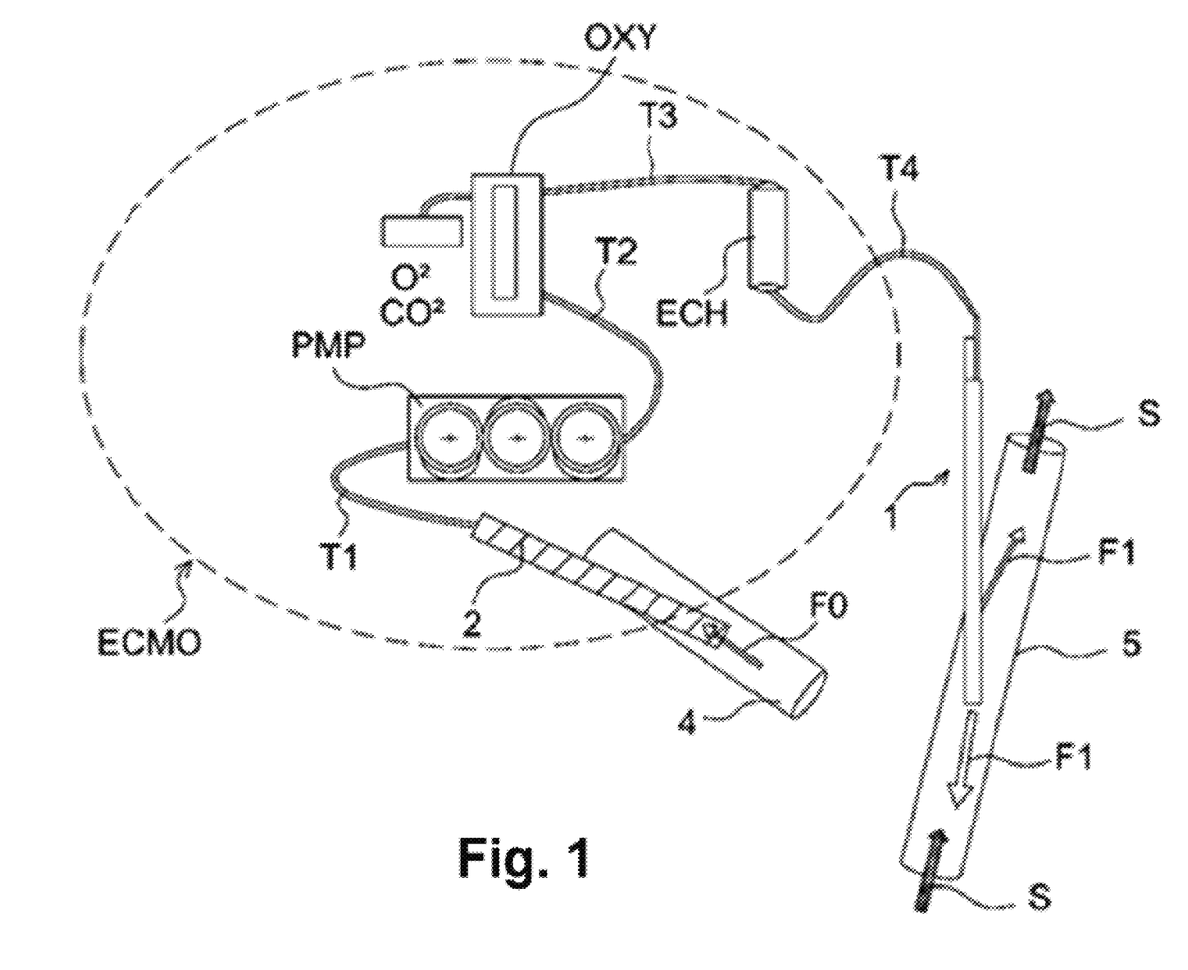
FIG. 1 shows a schematic representation of an ECMO system according to one embodiment of the invention.

FIG. 1 shows an ECMO system comprising an injection cannula according to the invention.

In reference to FIG. 1, the ECMO system comprises various components, in particular an intake cannula 2, a pump PMP, an oxygenator OXY, an injection cannula 1, and a heat exchanger ECH. In an alternative embodiment not shown here, the ECMO system does not comprise a heat exchanger.

The pump PMP performs a first function of pumping a volume of oxygen-poor, carbon dioxide-rich blood F0 from the intake cannula 2 inserted into a vein 4 of the patient. The volume of blood F0 is pumped at a flow rate that is predefined and possibly configurable. In particular, the flow rate must allow effective oxygenation and decarboxylation of the oxygen-poor, carbon dioxide-rich blood.

In addition, the pump PMP performs a second function of injecting a volume of oxygenated and decarboxylated blood F1 into the injection cannula 1 positioned in an artery 5 of the patient. Advantageously, the pump PMP is configured so that the blood injected into the injection cannula 1 reaches substantially the value of a physiological flow rate, depending on the patient's condition.

Furthermore, the pump PMP may be of the "centrifugal" type, i.e., it uses the rotational movement of a wheel inserted into the pump PMP. In an alternative embodiment, the pump PMP is a "roller" pump, also referred to as a "peristaltic" pump. Furthermore, the pump PMP can generate a pulsed flow rate.

According to an embodiment not shown here, the ECMO system comprises a reservoir which makes it possible to regulate the flow rate of treated blood. The flow of blood F0 extracted by the intake cannula 2 is then conveyed to the reservoir. Preferably, this step is carried out before the pumping step.

The oxygenator OXY is connected to the pump PMP from which it receives the oxygen-poor, carbon dioxide-rich blood F0 at a fixed flow rate. For this purpose, the oxygenator OXY comprises a membrane which artificially reproduces the function of the alveolocapillary membrane by carrying out gas exchanges making it possible to oxygenate the blood and remove the carbon dioxide contained in the blood.

According to one embodiment, the membrane of the oxygenator OXY is flat. Flat-membrane oxygenators OXY comprise silicone membranes or membranes assembled in layers. According to another embodiment, the membrane of the oxygenator OXY is tubular. The tubular membranes are composed of hollow fibres composed, for example, of non-porous polymethylpentenes. Advantageously, the fibres may comprise a coating offering less flow resistance and promoting laminar flow.

Furthermore, the heat exchanger ECH receives the volume of oxygenated and decarboxylated blood F1 from the oxygenator OXY in order to heat it before it reaches the injection cannula 1. In particular, the volume of blood F1 passes through a system that allows thermal energy to be transferred from a fluid such as water to the blood, without mixing the two fluids. The thermal flow passes through the exchange surface separating the oxygenated blood and the water. The heat exchanger ECH sets the temperature of the blood such that it is within the temperature range of the blood flowing in the patient's body.

The heat exchanger ECH may be integrated into the ECMO system or external to the latter. Furthermore, according to one embodiment, the heat exchanger ECH is connected to a reservoir so as to heat the blood after it has been drained; the steps of pumping and then oxygenation/decarboxylation are then carried out subsequently.

Alternatively, the volume of blood F1 may be heated by the oxygenator OXY itself. In this case, the oxygenator OXY advantageously comprises resistors provided for this purpose.

The intake cannula 2, the pump PMP, the oxygenator OXY, the heat exchanger ECH and the injection cannula 1 are interconnected via tubes T1, T2, T3 and T4. These tubes T1, T2, T3, T4 ensure the flow of blood, oxygenated or not, decarboxylated or not, heated or not, between the various components used to treat it. Thus, the first tube T1 allows the intake cannula 2 to be connected to the pump PMP. The second tube T2 allows the pump PMP to be connected to the oxygenator OXY. The third tube T3 allows the oxygenator OXY to be connected to the heat exchanger ECH and the fourth tube T4 allows the heat exchanger ECH to be connected to the injection cannula 1.

Advantageously, the diameter of the tubes T1, T2, T3, T4 is chosen so as to allow the blood to move while minimizing the risks of haemolysis and coagulation. In other words, the diameter of the tubes T1, T2, T3, T4 is adjusted according to the known flow rates allowing blood to flow in the body.

In addition, the tubes T1, T2, T3, T4 preferably have an anticoagulant coating, for example made from heparin, in order to prevent blood clots from forming inside the tubes T1, T2, T3, T4. Furthermore, the tubes T1, T2, T3, T4 may also have an anti-platelet aggregation coating in order to prevent platelet aggregation and inhibit thrombus formation.

Figure 2:
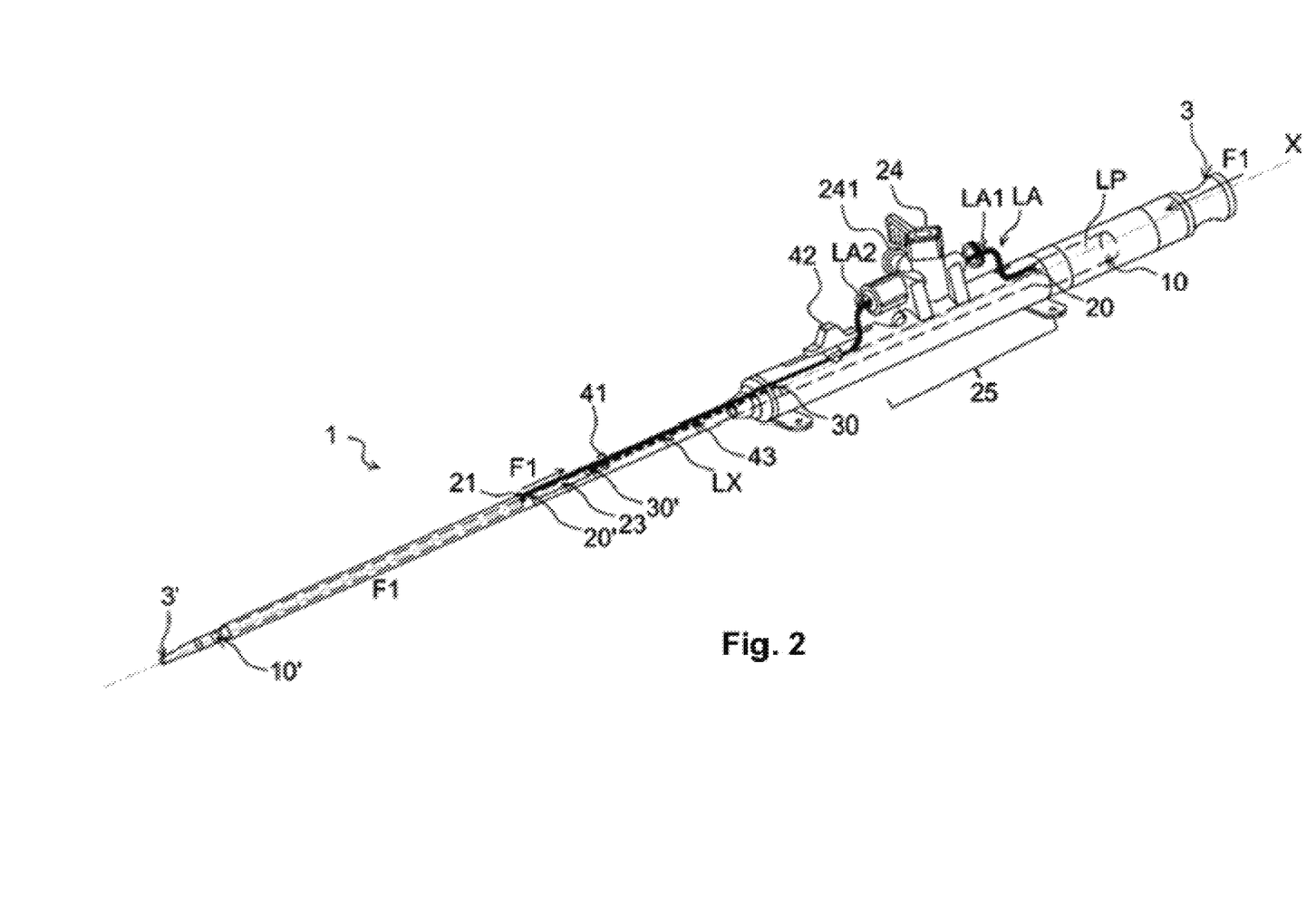
FIG. 2 shows an injection cannula according to one embodiment of the invention, used in the ECMO system shown in FIG. 1.

FIG. 2 shows a perspective view of the injection cannula 1 according to one embodiment of the invention, before it is inserted into the artery 5.

Figure 5:
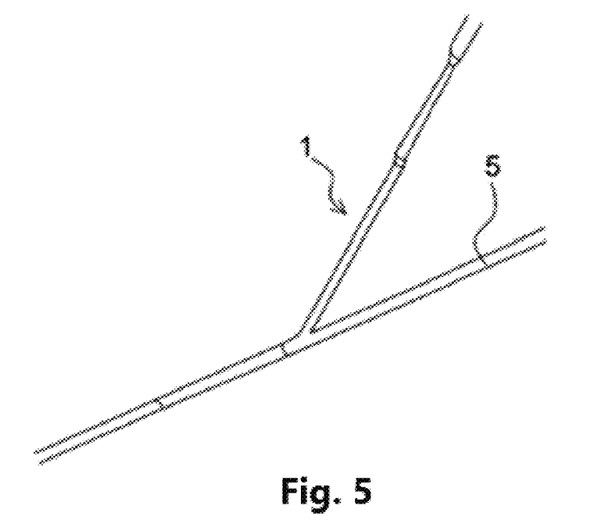
FIG. 5 is a diagram showing the introduction of the injection cannula of FIG. 2 into an artery.

FIG. 5 is a diagram showing the introduction of the injection cannula 1 of FIG. 2 into an artery 5.

Figure 6:
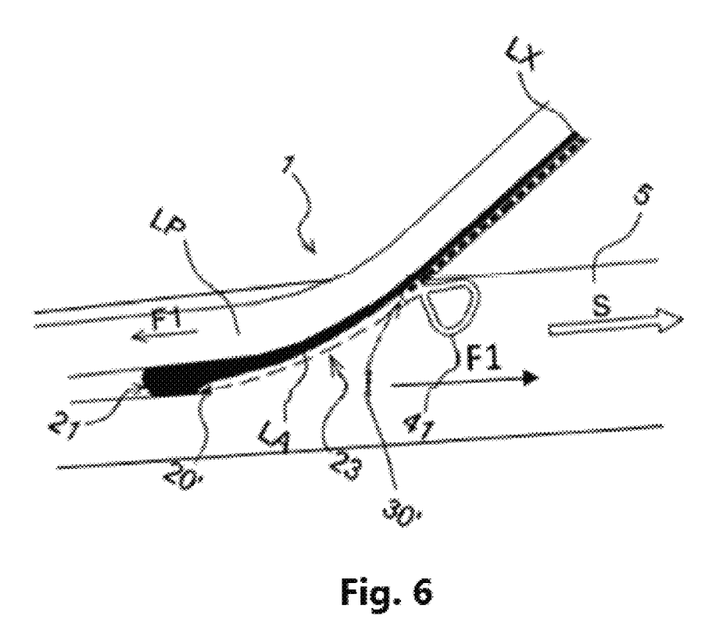
FIG. 6 shows an enlarged view of the injection cannula of FIG. 5, at the point of insertion of the cannula into the artery.

FIG. 6 is an enlarged view of the injection cannula 1 shown in FIG. 5, at the point of insertion of the cannula 1 into the artery 5.

When it is introduced into the artery 5, the injection cannula 1 is deformed such that it can be inserted transversely through the wall of the artery 5 and thus avoid causing damage to the wall of the artery 5. Advantageously, the injection cannula 1 is made from a deformable material, for example polyurethane. In addition, as can be seen in FIGS. 5 and 6, the injection cannula 1 is only partially introduced into the artery 5, a portion of the injection cannula 1 being kept outside the body of the patient in order to allow a practitioner to handle it.

With reference to FIG. 2, before it is inserted into an artery 5, the injection cannula 1 extends longitudinally along an axis X. In addition, the injection cannula 1 comprises an inlet 3 capable of cooperating with a connecting mouthpiece (not shown) of a component of the ECMO in order to receive the treated blood flow F1. Moreover, the injection cannula 1 comprises an outlet 3' intended to be inserted into the artery 5.

Furthermore, the injection cannula 1 comprises a main lumen LP, an accessory reperfusion lumen LA and an auxiliary lumen LX delimiting three spaces of the injection cannula 1.

The main lumen LP injects the blood flow F1 coming from the inlet 3 of the injection cannula 1 into the artery 5, in a first direction, in this case a retrograde direction. To this end, the main lumen LP extends along the injection cannula 1 and comprises an inlet 10 and an outlet 10'. The inlet 10 of the main lumen LP is arranged downstream of the inlet 3 of the injection cannula 1 in order to receive the blood flow F1. The blood flow F1 is then discharged via the outlet 10' of the main lumen LP arranged upstream of the outlet 3' of the injection cannula 1.

Furthermore, the main lumen LP has a circular cross-section and has a diameter that varies between the inlet 10 and the outlet 10' of said main lumen LP. Also, the diameter of the main lumen LP at its outlet 10' is smaller than at its inlet 10 so that the part of the injection cannula 1 intended to be inserted into the artery 5 is adapted to the diameter of said artery 5. Moreover, such a reduction in the diameter of the main lumen LP makes it possible to accelerate the injected flow rates and therefore to reduce the hydrodynamic force to be supplied by the ECMO system. Advantageously, the diameter of the main lumen LP is between 10 F and 21 F, i.e., between 3.3 mm and 7 mm. Naturally, the diameter of the main lumen LP may be constant along the main lumen LP. In addition, it is quite possible for the main lumen LP to have a non-circular cross-section, for example an oval, elliptical cross-section.

The accessory reperfusion lumen LA injects a portion of the blood flow F1 into the artery 5 in a second direction, in this case an anterograde direction. For this purpose, the accessory reperfusion lumen LA has an inlet 20 in fluidic communication with the main lumen LP. In particular, the inlet 20 of the accessory reperfusion lumen LA is arranged downstream of the inlet 10 of the main lumen LP in order to collect a portion of the blood flow F1 coming from the main lumen LP. In an alternative embodiment, the inlet 20 of the accessory reperfusion lumen LA is not in fluid communication with the main lumen LP. In this case, the accessory reperfusion lumen LA collects a portion of the blood flow F1 directly from the inlet 3 of the injection cannula 1. Furthermore, as can be seen in FIG. 2, a portion of the accessory reperfusion lumen LA extends parallel to the main lumen LP.

Figure 4:
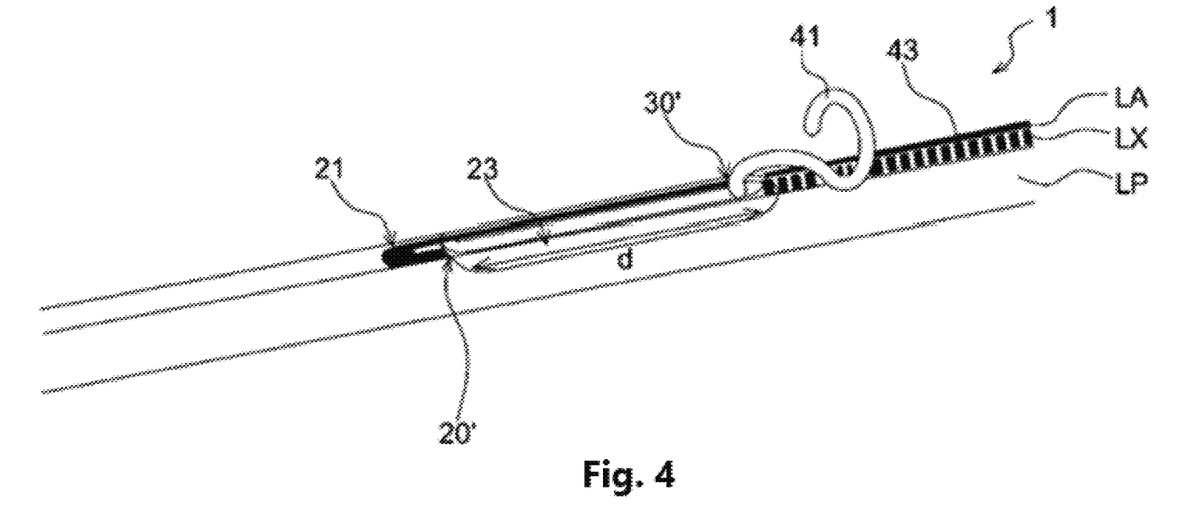
FIG. 4 is an enlarged view of the injection cannula shown in FIG. 2, at the stop.

Moreover, the accessory reperfusion lumen LA comprises an angled portion 21 making it possible to modify the retrograde direction of flow of the blood flow F1 collected by the accessory reperfusion lumen LA. The angled portion 21 allows the collected blood flow F1 to flow in an anterograde direction. As can be seen in FIG. 4, the angled portion 21 forms an arc of a circle, or even a semicircle, allowing the orientation of the fluid F1 to be modified in an anterograde direction, i.e., in a direction opposite to the direction in which the blood flow F1 is ejected at the outlet 10' of the main lumen LP.

The accessory reperfusion lumen LA further comprises an outlet 20' opening into a lateral opening 23 provided in the injection cannula 1 so as to discharge the blood flow F1 flowing in an anterograde direction into the artery 5.

Unlike the main lumen LP, the accessory reperfusion lumen LA, which also has a circular cross-section, has a constant diameter along its entire length. According to one embodiment, the accessory reperfusion lumen LA has a diameter of between 20 G, i.e., 0.8 mm, and 6 F, i.e., 2 mm. Naturally, the diameter of the accessory reperfusion lumen LA may vary between the inlet 20 and the outlet 20' of the accessory reperfusion lumen LA. It should be noted that it is possible to vary the ratio of the cross-sections of the lumens LA and LP in order to control the speed and the flow rate at which the blood flow F1 is ejected into the artery 5 in the two directions, i.e., anterograde and retrograde. Furthermore, the accessory reperfusion lumen LA may have a non-circular cross-section, for example an oval, elliptical cross-section.

In an alternative embodiment not shown here, the accessory reperfusion lumen LA is integrated into the main lumen LP as described in patent application FR 1661037. In this case, the outlet 20' of the accessory reperfusion lumen LA also opens into the lateral opening 23 provided in the injection cannula 1. In an alternative embodiment not shown here, the outlet 20' of the accessory reperfusion lumen LA is equipped with an electromechanical flow-measuring device connected to an electronic display located at the handle, i.e., at the inlet 3, of the injection cannula 1.

Furthermore, a bleed valve 24 is connected to the accessory reperfusion lumen LA in order to bleed it. In particular, the bleed valve 24 is a three-way valve in which two channels are connected to two portions LA1, LA2 of the accessory reperfusion lumen LA while one channel forms an outlet 241. It should be noted that the part of the injection cannula 1 comprising the bleed valve 24 is intended to be kept outside the body of the patient.

The bleed valve 24 allows two channels to be opened and the third channel to be closed, simultaneously. Thus, when the outlet 241 of the bleed valve 24 is closed, the blood flow F1 flowing in the accessory reperfusion lumen LA can pass from the inlet 20 of the accessory reperfusion lumen LA to the outlet 20' of the accessory reperfusion lumen LA. Furthermore, when the outlet 241 of the bleed valve 24 is open, the blood flow F1 cannot pass from the inlet 20 of the accessory reperfusion lumen LA to the outlet 20' of the accessory reperfusion lumen LA.

When the bleed valve 24 is in a first position, referred to as the anterograde bleed or flow control position, the blood flow F1 flows in the accessory reperfusion lumen LA from upstream to downstream, i.e., from the inlet 20 of the accessory reperfusion lumen LA to the outlet 241 of the bleed valve 24.

When the bleed valve 24 is in a second position, referred to as the retrograde bleed or reflux control position, the blood flow F1 flows in the accessory reperfusion lumen LA from downstream to upstream, i.e., from the outlet 20' of the accessory reperfusion lumen LA to the outlet 241 of the bleed valve 24. It should be noted that the blood flow F1 flowing in the accessory reperfusion lumen LA from downstream to upstream can be generated when the injection cannula 1 is introduced into the artery 5.

Advantageously, the bleed valve 24 helps ensure that the outlet 20' of the accessory reperfusion lumen LA is correctly positioned in the artery 5. To this end, the flow and the reflux between the outlet 20' of the accessory reperfusion lumen LA and the outlet 241 of the bleed valve 24 are tested by using a syringe connected to the outlet 241 of the bleed valve 24 in order to respectively inject or suck a fluid between the outlet 20' of the accessory lumen LA and the outlet 241 of the bleed valve 24.

Furthermore, in order to ensure effective reperfusion of the artery 5, it is essential that the outlet 20' of the accessory reperfusion lumen LA be positioned in the artery 5 so that the blood flow F1 flowing in an anterograde direction is ejected into the middle of the lumen of the artery 5. In other words, the outlet 20' of the accessory reperfusion lumen LA must not be positioned facing an anterior, posterior or lateral wall of the artery 5.

To this end, the injection cannula 1 comprises a device for positioning the injection cannula 1 in the artery 5 which allows the injection cannula 1 to be locked in position in the artery 5. In addition, the outlet 30' of the auxiliary lumen LX is positioned at a predetermined distance d from the outlet 20' of the accessory reperfusion lumen LA so that, when the injection cannula 1 is locked in position in the artery 5, the blood flow F1 that flows in the accessory reperfusion lumen LA is discharged correctly into the artery 5, i.e., in the anterograde direction. Advantageously, the predetermined distance d between the outlet 30' of the auxiliary lumen LX and the outlet 20' of the accessory reperfusion lumen LA is between 0.1 and 500 mm.

In order to lock the position of the injection cannula 1 in the artery 5, the positioning device comprises a stop 41 designed to move along an auxiliary lumen LX and be deployed in the artery 5.

The auxiliary lumen LX extends parallel to the main lumen LP and has an inlet 30 and an outlet 30'. The outlet 30' of the auxiliary lumen LX, arranged upstream of the outlet 20' of the accessory reperfusion lumen LA, opens into the lateral opening 23 provided in the injection cannula 1. In an alternative embodiment, the outlet 30' of the auxiliary lumen LX and the outlet 20' of the accessory reperfusion lumen LA do not open into the same lateral opening of the injection cannula 1.

In addition, the auxiliary lumen LX has a circular cross-section and has a constant diameter along its entire length, for example a diameter of between 20 G and 6 F, i.e., between 0.8 and 2 mm. In an alternative embodiment, the diameter of the auxiliary lumen LX varies between the inlet 30 and the outlet 30' of the auxiliary lumen LX. It should also be noted that the auxiliary lumen LX may have a non-circular cross-section, for example an elliptical cross-section.

The movement of the stop 41 along the auxiliary lumen LX and then its deployment in the artery 5 are controlled remotely by movement means intended to be kept outside the body of the patient. In particular, the movement means allow the stop 41 to be moved via a connecting element 43, connected to the stop 41, capable of moving along the auxiliary lumen LX.

Figure 3:
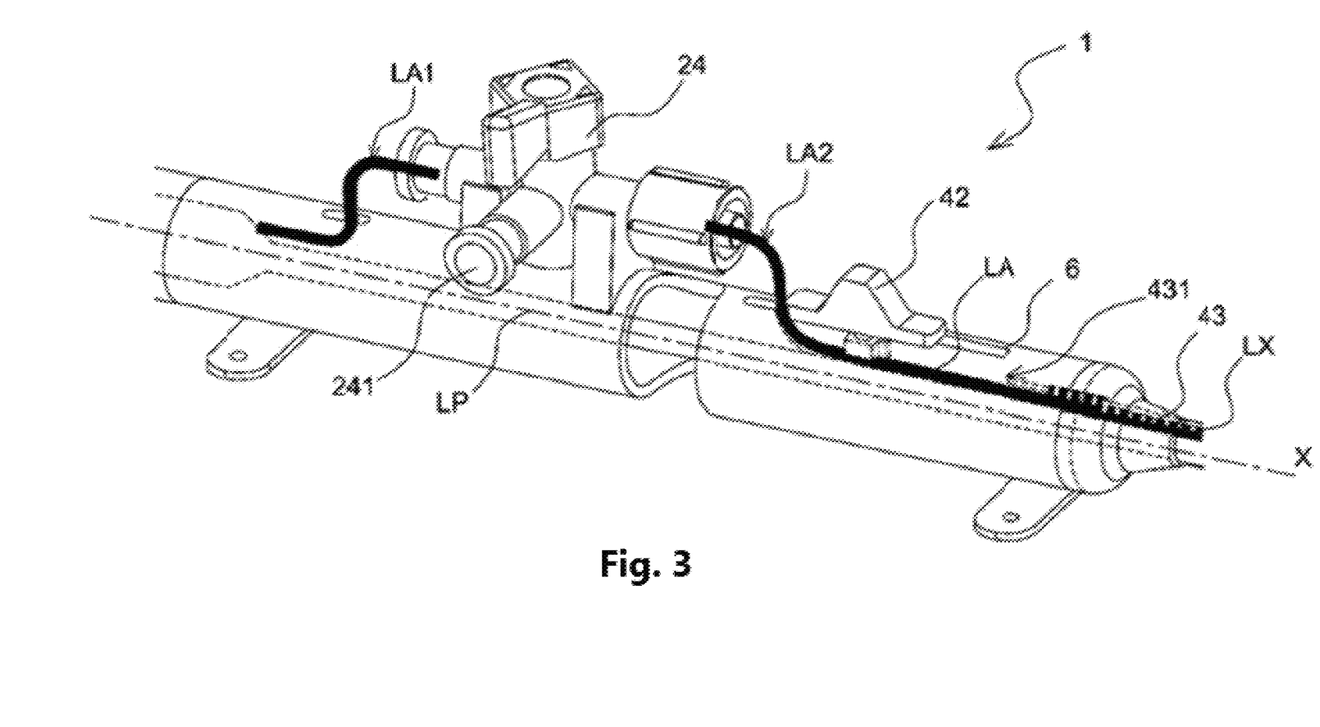
FIG. 3 is an enlarged view of the injection cannula shown in FIG. 2, at the stop movement means.

FIG. 3 is an enlarged view of the injection cannula 1 at the stop 41 movement means.

According to the embodiment shown in FIGS. 2 and 3, the movement means are formed by a push-button 42 designed to slide along a longitudinal groove 6 provided in the main lumen LP. The movement of the push-button 42 in the longitudinal groove 6, from upstream to downstream, causes the connecting means 43 and therefore of the stop 41 to be moved in the same direction. In particular, as the push-button 42 moves from upstream to downstream, it comes into contact with one end 431 of the connecting means 43 and then pushes the connecting means 43 and the stop 41 towards the artery 5. At the outlet 30' of the auxiliary lumen LX, the stop 41 is deployed in the artery 5. In an alternative embodiment, the stop 41 is deployed by means of an electric motor located at the handle of the injection cannula 1, controlled by a switch also located at said handle.

FIG. 4 is an enlarged view of the injection cannula 1 at the stop 41.

The shape and dimensions of the stop 41 are chosen such that, once the stop 41 has been deployed in the artery 5, the injection cannula 1 cannot be removed from the artery 5. As can be seen in FIGS. 4 and 6, the deployed stop 41 extends in the upstream direction of the injection cannula 1, forming an elbow with the connecting means 43 that allows the position of the injection cannula 1 to be locked in the artery 5. In particular, after the stop 41 has been deployed in the artery 5, the injection cannula 1 must be pulled out of the artery 5 until the stop 41 comes to bear against the inner face of the anterior wall of the artery 5. In this position, the stop 41 prevents the injection cannula 1 from being removed from the artery 5. The terms "anterior" and "posterior" are used respectively to denote a front part and a rear part of a cavity or organ of the human body in anatomical position.

Advantageously, the stop 41 is made from a shape memory material, i.e., the material has the ability to remember an initial shape and to return to its initial shape even after being deformed. Thus, the stop 41 is designed to be deformed when it passes through the auxiliary lumen LX and to return to its initial shape when it is outside the auxiliary lumen LX, in particular inside the artery 5.

In addition, the shape of the stop 41 is chosen so as not to cause damage to the artery 5 while having tensile strength. Advantageously, the stop 41 has rounded corners and a compact shape. Furthermore, the shape of the stop 41 may vary in order to obtain the best strength with the smallest space requirement and the least aggression to the wall of the artery 5.

Preferably, the stop 41 and/or the connecting means 43 are made from a nickel-titanium alloy wire, because this has good rigidity. In addition, the stop 41 may have an anti-thrombogenic coating, i.e., an anti-coagulant and/or anti-platelet aggregation coating, and/or an anti-proliferative coating.

Furthermore, in order to remove the injection cannula 1 from the artery 5, it is sufficient to move the push-button 42 from downstream to upstream, which results in the withdrawal of the stop 41, which is deformed before being reintroduced into the auxiliary lumen LX.

Advantageously, the stop 41 has a radio-opaque or echo-opaque marking designed to allow the stop 41 to be identified by radiography or echography. According to another embodiment, the identification marking is made on the outlet 30' of the auxiliary lumen LX. In another alternative embodiment, the stop 41 and the outlet 30' of the auxiliary lumen LX are both marked.

The invention also relates to an ECMO system comprising the injection cannula 1 according to the invention.

What is claimed is:

1. A cannula for injecting a fluid into a cavity of the human or animal body, comprising:
    a main lumen defining a first space of the cannula for the fluid to flow in a first direction; and
    an accessory reperfusion lumen defining a second space of the cannula and comprising:
        an inlet for collecting a portion of the fluid flowing in the first direction;
        an angled portion for changing the direction of flow of the fluid collected by the accessory reperfusion lumen; and
        an outlet for discharging the collected fluid in a second direction into the cavity;
    a stop configured to move along an auxiliary lumen so as to position the cannula in the cavity, the auxiliary lumen (LX) defining a third space of the cannula and comprising an outlet opening into the cavity; and a connector connected to the stop and extending along the auxiliary lumen, the stop being further configured to be deployed in the cavity, via the outlet of the auxiliary lumen, in order to ensure that the cannula is locked in position in the cavity, the outlet of the auxiliary lumen being arranged at a predetermined distance from the outlet of the accessory reperfusion lumen such that when the stop locks the cannula in position in the cavity, the outlet of the accessory reperfusion lumen is oriented in the cavity such that the collected fluid is discharged in the second direction, wherein the connector is configured to move the stop along the auxiliary lumen.

2. The cannula according to claim 1, wherein the predetermined distance between the outlet of the auxiliary lumen and the outlet of the accessory reperfusion lumen is between 0.1 and 500 mm.

3. The cannula according to claim 1, wherein the stop is configured to be moved via a push-button capable of moving in a longitudinal groove provided in the cannula, the movement of the push-button in the longitudinal groove causing the stop to be moved along the auxiliary lumen.

4. The cannula according to claim 1, wherein the deployed stop has a shape and dimensions designed to prevent the cannula from being withdrawn when inserted inside the cavity.

5. The cannula according to claim 1, wherein the stop is made from a shape memory material.

6. The cannula according to claim 1, wherein the stop is made from a nickel-titanium alloy wire.

7. The cannula according to claim 1, wherein the deployed stop is diamond-shaped.

8. The cannula according to claim 1, wherein the stop has an anti-thrombogenic and/or anti-proliferative coating.

9. The cannula according to claim 1, wherein the stop and/or the outlet of the auxiliary lumen has/have a radio-opaque or echo-opaque marking designed to allow said stop and/or the outlet of said auxiliary lumen to be identified by radiography or echography.

10. The cannula according to claim 1 further comprising a bleed valve connected to the accessory reperfusion lumen.

11. A system for injecting a fluid into a cavity of the human or animal body, comprising:

an intake cannula for receiving a predetermined fluid;

a pump for pumping the predetermined fluid coming from the intake cannula;

an oxygenator for oxygenating the predetermined fluid coming from an outlet of the pump; and the cannula according to claim 1 for injecting the oxygenated fluid into the cavity.

* * * * *